United States Patent
Robran

(10) Patent No.: US 11,737,943 B2
(45) Date of Patent: Aug. 29, 2023

(54) CUSHION FOR MEDICAL INSTRUMENT STAND

(71) Applicant: BONE FOAM INC., Corcoran, MN (US)

(72) Inventor: Chad Robran, Plymouth, MN (US)

(73) Assignee: Bone Foam, Inc., Corcoran, MN (US)

( * ) Notice: Subject to any disclaimer, the term of this patent is extended or adjusted under 35 U.S.C. 154(b) by 359 days.

(21) Appl. No.: 16/816,104

(22) Filed: Mar. 11, 2020

(65) Prior Publication Data

US 2020/0289355 A1 Sep. 17, 2020

Related U.S. Application Data

(60) Provisional application No. 62/817,282, filed on Mar. 12, 2019.

(51) Int. Cl.
*A61G 13/12* (2006.01)

(52) U.S. Cl.
CPC ......... *A61G 13/126* (2013.01); *A61G 13/124* (2013.01); *A61G 13/1235* (2013.01); *A61G 13/1245* (2013.01)

(58) Field of Classification Search
CPC .............. A61G 13/126; A61G 13/1235; A61G 13/124; A61G 13/1245; A61G 13/12; A61G 13/1205; A61G 13/125; A61B 50/15; A61B 2050/155
See application file for complete search history.

(56) References Cited

U.S. PATENT DOCUMENTS

| | | | |
|---|---|---|---|
| 2,324,619 A * | 7/1943 | Dunn | A61G 7/0755 5/81.1 R |
| 2,732,269 A * | 1/1956 | Astroff | A61G 13/12 5/648 |
| 2,871,074 A * | 1/1959 | Malerich, Jr. | A61G 13/12 5/648 |
| 3,083,376 A | 4/1963 | Johns | |
| 3,738,405 A | 6/1973 | Ericson | |

(Continued)

FOREIGN PATENT DOCUMENTS

| CN | 108904208 A * | 11/2018 | A61B 90/14 |
|---|---|---|---|
| EP | 1785124 A2 * | 5/2007 | A61B 6/0442 |
| WO | WO-2015019189 A2 * | 2/2015 | A61B 17/02 |

OTHER PUBLICATIONS

International Search Report and Written Opinion received for PCT Patent Application No. PCT/US2020/022456, dated Jun. 10, 2020, 12 pages.

*Primary Examiner* — David R Hare
*Assistant Examiner* — Alison N Labarge
(74) *Attorney, Agent, or Firm* — Workman Nydegger

(57) ABSTRACT

A cushion device is configured to be positioned upon a tray of a medical instrument stand such as a Mayo stand. The cushion device includes an upper portion, a front portion that connects to a front side of the upper portion and extends downward therefrom, and first and second side portions that connect to respective first and second longitudinal sides of the upper portion and extend downward therefrom. The inner surfaces of the upper portion, front portion, and side portions define a hollow receptacle that is configured in size and shape to receive a tray of a medical instrument stand so that the cushion device can be selectively positioned on the medical instrument stand.

20 Claims, 5 Drawing Sheets

(56) References Cited

U.S. PATENT DOCUMENTS

| | | | |
|---|---|---|---|
| 4,265,232 A | 5/1981 | Stonich | |
| 5,149,033 A | 9/1992 | Burzler | |
| 5,379,703 A | 1/1995 | Marshall | |
| 5,603,692 A | 2/1997 | Maxwell | |
| 5,871,015 A | 2/1999 | Lofgren et al. | |
| 6,195,820 B1 * | 3/2001 | Heimbrock | A61G 13/0045 403/68 |
| 6,405,389 B1 | 6/2002 | Harty | |
| 6,463,309 B1 | 10/2002 | Ilia | |
| 8,904,583 B1 * | 12/2014 | Cavitt | A61G 13/129 5/621 |
| 2003/0056698 A1 | 3/2003 | Comeaux | |
| 2004/0171923 A1 * | 9/2004 | Kalafut | A61B 5/0059 600/407 |
| 2007/0271701 A1 * | 11/2007 | Diaz | A61G 13/0063 5/621 |
| 2011/0179577 A1 | 7/2011 | Gould et al. | |
| 2011/0180436 A1 | 7/2011 | von Posern | |
| 2014/0190488 A1 * | 7/2014 | Robran | A61G 99/00 128/845 |
| 2015/0320928 A1 * | 11/2015 | Allen | A61G 13/124 604/356 |
| 2015/0351707 A1 | 12/2015 | Sampognaro | |
| 2016/0250039 A1 | 9/2016 | Chow | |
| 2016/0296031 A1 * | 10/2016 | Sramek | A61F 5/56 |
| 2019/0083345 A1 * | 3/2019 | Romano | A61G 13/1285 |
| 2019/0133862 A1 * | 5/2019 | Norris | A61G 13/0036 |

* cited by examiner

CUSHION FOR MEDICAL INSTRUMENT STAND

CROSS-REFERENCE TO RELATED APPLICATIONS

This application claims priority to, and the benefit of, U.S. Provisional Patent Application Ser. No. 62/817,282, filed on Mar. 12, 2019 and titled "Cushion for Medical Instrument Stand," which is incorporated herein by this reference in its entirety.

BACKGROUND

Medical instrument stands, often referred to as "Mayo stands", are ubiquitous in medical facilities and provide many uses. Mayo stands are portable stands that are configured with a tray supported by a base. The tray may be utilized to hold surgical instruments and materials during operating room and in-office procedures. Mayo stands are popular in healthcare facilities because they offer a convenient location that can be easily sterilized and positioned near the patient during procedures without inhibiting access to the patient or other equipment.

Typically, the height of the stand can be adjustable. The tray of the stand may be removable for easier cleaning and sterilization. The Mayo stand may be fitted with wheels or a rolling base to aid in maneuverability of the stand to the desired location within the operating room or medical office. Mayo stands come in a wide variety of sizes and configurations to accommodate specific medical practices.

In addition to requiring close and quick access to medical instruments, there are many other items and procedures associated with different medical practices that require quick and easy solutions. Some surgeries and other procedures are performed only after extensive planning and use large, sometimes cumbersome, equipment to help position a patient or the patient's extremities for the procedure. A standard operating surface can include a medical table, a hospital bed, or a type of reclining chair. These are usually found in hospitals, but less equipment is usually available for in-office procedures that may also benefit from more adjustable or robust equipment.

In some cases, a doctor may find that repositioning a portion or extremity of the patient's body during surgery would be beneficial for a certain step or certain number of steps. It is difficult to obtain, transfer or move either the equipment or the patient after the surgery or other medical procedure has been started. Sometimes, doctors look for ad-hoc ways to overcome the limitations of the standard equipment found in the operating room or office. However, there are limited to no equipment or devices available having surfaces conducive to acting as operating or procedural surfaces for soft-tissue contact (e.g., metal or very hard plastics are unsuitable for direct contact with skin, especially with any pressure from the weight of the extremity).

Thus, there is a persistent and on-going need for improved devices and methods for patient positioning for some surgeries and procedures whether performed in a hospital or in the doctor's office.

BRIEF SUMMARY

Embodiments disclosed herein relate to a specialized type of cushion device that allows for a standard medical instrument stand (e.g., Mayo stand) to be converted to a cushioned operating or positioning surface for a patient.

In some embodiments, the cushion device is configured for placement on a medical instrument stand. The cushion device includes an upper portion having a front side, a rear side, first and second longitudinal sides, an upper surface, and a bottom surface. The cushion device also includes a front portion connected to the front side of the upper portion and extending downwards therefrom. The first and second side portions each connect respectively to the first and second longitudinal sides of the upper portion and extending downward therefrom. A hollow receptacle is defined by the front portion, the first and second side portions, and by the bottom surface of the upper portion. The hollow receptacle is configured in size and shape to receive a medical instrument tray. Embodiments herein also relate to a method to cushion a medical instrument tray.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

A more particular description will be rendered by the embodiments illustrated in the appended drawings. It is appreciated that these drawings depict only exemplary embodiments of the disclosure and are therefore not to be considered limiting of its scope. In the accompanying drawings.

DETAILED DESCRIPTION

Introduction

In some instances, medical instrument stands (e.g., Mayo stands) may be used to at least partially support a patient's limb during a procedure. For example, a limb may be moved so as to extend off of the operating table, and the medical instrument stand may be positioned next to the operating table in order to support the limb. This allows for customizable use of the medical instrument stand and gives the medical practitioner flexibility in organizing and positioning the patient during the procedure.

However, use of a medical instrument stand in this manner is associated with several limitations. The hard surface of the tray does not provide good cushioning of the patient's limb. Further, portions of the patient's limb may be impinged by portions of the tray as the limb is laid across the tray. This can create pressure points leading to sores or even serious tissue damage, particularly given the fact that some procedures may last hours, during which time the patient is unconscious and unable to move or respond to pain indicators.

The present disclosure relates to cushion devices configured to adapt a medical instrument stand (e.g., Mayo stand) and allow the medical instrument stand to be effectively utilized for supporting a patient's limb or otherwise interfacing with the patient. The cushion devices described herein allow for these beneficial uses while avoiding the limitations that accompany such uses with a non-adapted Mayo stand.

Overview of Medical Instrument Stand

Figure 1:
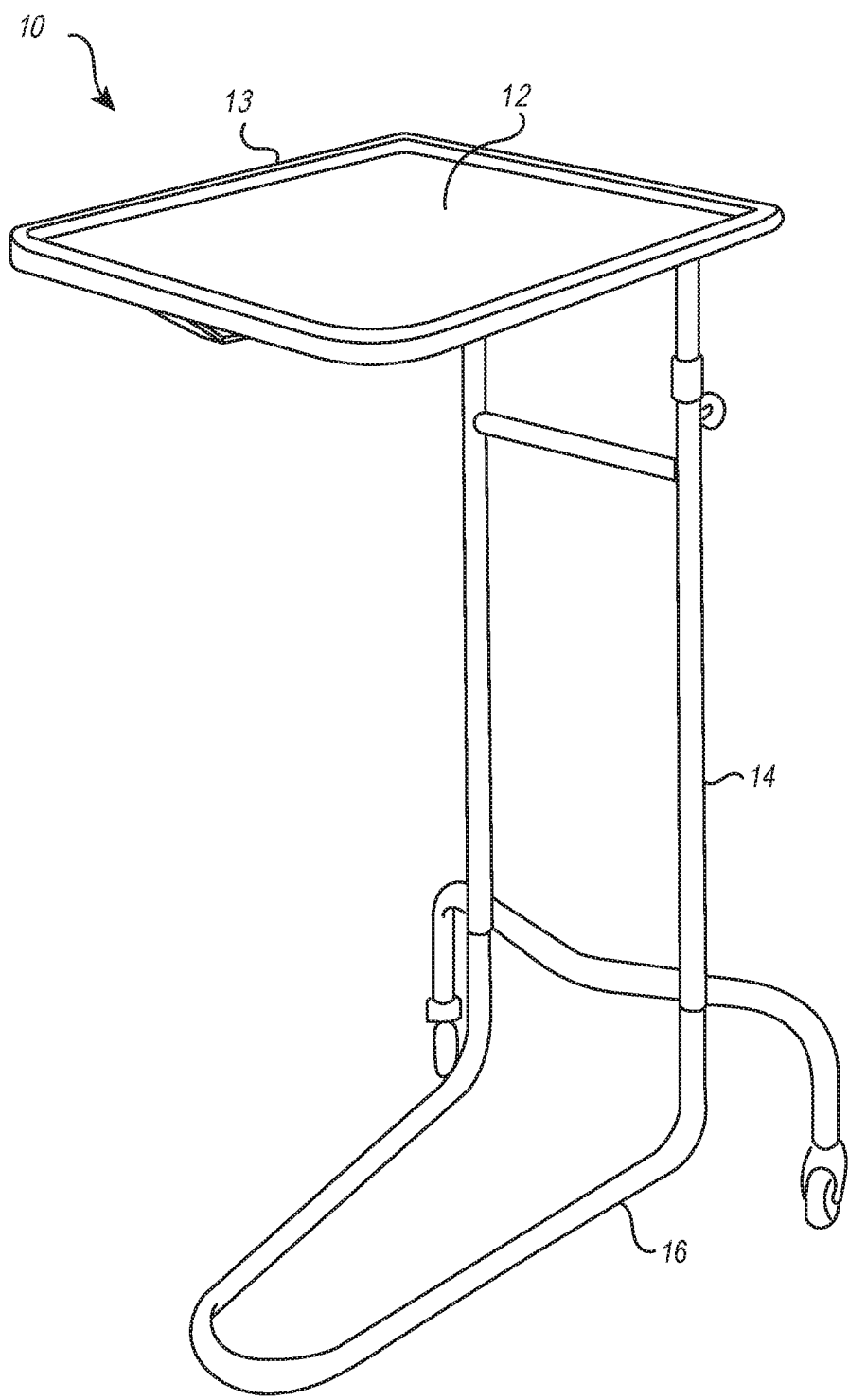
FIG. 1 illustrates a perspective view of a conventional medical instrument stand.

FIG. 1 illustrates a conventional medical instrument stand 10 (an example of which is often referred to in the art as a "Mayo stand"). The medical instrument stand 10 includes an instrument tray 12 supported by a vertical member 14 (or sometimes multiple posts or other vertical members) connected to a base 16. The instrument tray 12 may be removable or may be a component integral to the stand 10. The vertical member 14 is often adjustable so that the height of the tray 12 above the floor can be adjusted. Often, the base 16 includes wheels to provide easy movement of the stand 10, though some models may omit wheels and be configured to be simply slid across the floor to a desired position.

In use, the instrument stand 10 is usually positioned over or adjacent to a surgical site. The tray 12 then provides a place for instruments and/or supplies used during an operating room or in-office procedure. The tray 12 is usually removeable to allow for easy cleaning and maintenance. Such stands 10 are ubiquitous throughout medical facilities because of the many benefits provided, including minimizing wasted space in the operating room, mobility, customizable organization and use, durability, and ease of cleaning.

On at least some occasions, the stand 10 may also be used to prop a patient's limb during a procedure. For example, if a patient's arm needs to be extended away from the body and off the operating table during a procedure, the instrument stand 10 may be positioned next to the table to support or help support the arm. In other situations, the patient's leg may be extended off the operating table and supported at least in part by the stand 10.

Easy positioning of the stand 10 beneficially allows these types of custom uses of the stand 10 during a procedure. However, propping a patient's limb as "dead weight" upon the tray 12, which is typically formed of rigid metal, is associated with limitations. For example, the hard surface of the tray 12 does not provide good cushioning of the patient's limb. Further, the rim portion 13 of the tray 12 necessarily sticks up and can impinge against portions of the patient's limb laid across it. This can create pressure points leading to sores or even serious tissue damage, particularly given the fact that some procedures may last hours, during which time the patient is unconscious and unable to move or respond to pain indicators.

Overview of Exemplary Cushion Device

Figure 2:
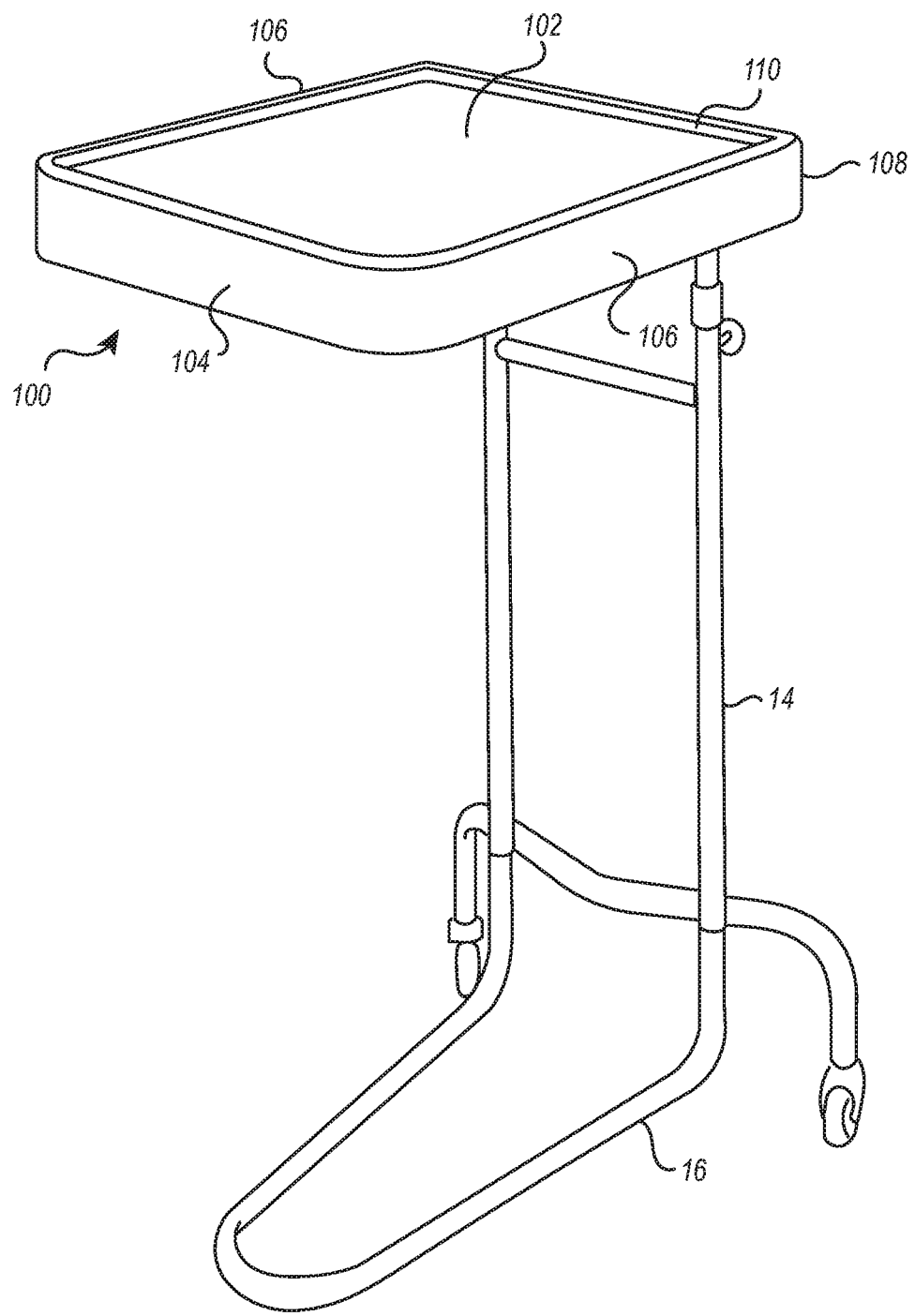
FIG. 2 illustrates a perspective view of a medical instrument stand having a cushion device positioned thereon.

FIG. 2 illustrates the instrument stand 10 of FIG. 1 with a cushion device 100 positioned thereon. As shown, the cushion device 100 is configured to be selectively placed upon the tray 12 of the stand 10 of FIG. 1 and/or upon a portion of the frame of the stand 10 underlying the tray 12 (e.g., if the tray is removed before placement of the cushion device). This portion of the frame of the medical instrument stand associated with the tray and/or underlying the tray (e.g., the portion that the tray connects to) may be referred to herein as the "upper frame." Most examples will be described herein in the context of positioning the cushion device 100 upon the tray 12, but it will be understood that the same description applies to applications where the cushion device 100 is placed directly upon the frame of the stand 10 associated with the tray. The cushion device 100 is beneficially formed of a relatively soft, cushioning material that provides greater comfort, safety, and support to a limb positioned thereon.

In embodiments where the cushion device 100 is placed on the upper frame of stand 10 with the tray 12 removed, the cushion device 100 can advantageously have sufficient firmness or stiffness to span between the upper frame and support a limb and/or instruments without collapsing, such as by selection of cushion material of sufficient firmness or stiffness and/or providing an external or internal rigid or semi-rigid frame (not shown) e.g. of plastic, metal, and/or wood.

In some embodiments, the cushion device 100 may be formed from a polymer foam material, such as an open or closed cell foam, a "memory foam" (e.g., low-resilience polyurethane foam and/or other viscoelastic foams), rubber materials, gel padding, or combinations thereof. Some embodiments may also include a water-resistant coating, such as a flexible, water-resistant polymer (e.g., vinyl-based) that coats the foam material and allows for easy cleaning of the cushion device 100. Some embodiments may include an external or internal frame (not shown).

Some embodiments may additionally or alternatively include a removeable "skin", such as a fabric or sterile sheet material, and may optionally include one or more zippers, hook and loop fasteners, buttons, snaps, and/or other means of donning and doffing the removeable skin. The removeable skin, for example, may be changed from patient to patient and/or from procedure to procedure for sanitary reasons and/or to reduce the amount of cleaning required. The skin may also be configured as a sterile bag. Additionally, or alternatively, the removeable skin may be configured as continuous roll of a sterile covering or sheet.

In some embodiments, the cushion device 100 is radiolucent. As used herein, the term "radiolucent" means that the device 100 allows substantial passage of imaging radiation (e.g. x-rays) and therefore allows for significant imaging contrast against other materials known to be more radiopaque in this context, such as bones, metal implants, and the like.

In certain applications of the cushion device 100, the cushion device 100 may be configured to be removably secured to a stand 10 with its tray 12 removed. The cushion device 100 is able to fit onto the frame (not shown, but implied) that typically supports the tray 12 but can also support and stabilize the cushion device 100 even without the tray 12. Thus, when used with a stand 10 having its tray 12 removed, the cushion device 100 can offer a radiolucent operating surface that is secured around the frame that usually supports the tray 12. In other cases, such as where the tray 12 is radiolucent, the radiolucent cushion device 100 can be fitted onto the radiolucent tray 12 to provide a cushioned radiolucent operating and/or positioning surface. This is especially beneficial where the limbs or body must be positioned in a specific manner for effective imaging (e.g., for taking x-rays).

As shown in FIG. 2, the cushion device 100 may include a front portion 104, two side portions 106 that connect to the front portion 104 and extend longitudinally therefrom, and an upper portion 102 supported by the front portion 104 and side portions 106. The cushion device 100 may also include a back portion 108 (better shown in FIG. 5) which connects to the side portions 106 and is disposed opposite the front portion 104.

The cushion device 100 may also include a rim 110 that extends along at least a portion of the upper portion 102, preferably along the entire perimeter. The rim is preferably formed with a rounded "speedbump" cross-sectional shape that omits sharp corners. In addition to this shape, the soft (e.g., foam) construction of the components of the device help to provide good, cushioned support that limits or avoids pressure points on a limb positioned thereon. The rim 110 can also function to preserve the tray-like functionality of the stand 10. That is, the rim 110 allows the cushion device 100 to be used for holding instruments and/or supplies (e.g., preventing them from falling) in the same fashion as the typical metal tray 12. In other words, the rim 110 functions to prevent instruments from rolling off the edge of the cushion device 100.

The bottom of the cushion device 100 is preferably open so that the device can be readily positioned over the tray 12 of the stand 10 and lowered onto the tray 12. That is, when the cushion device 100 is positioned, the tray 12 is received into a hollow receptable defined by at least the upper portion 102, front portion 104, and side portions 106.

Figure 3:
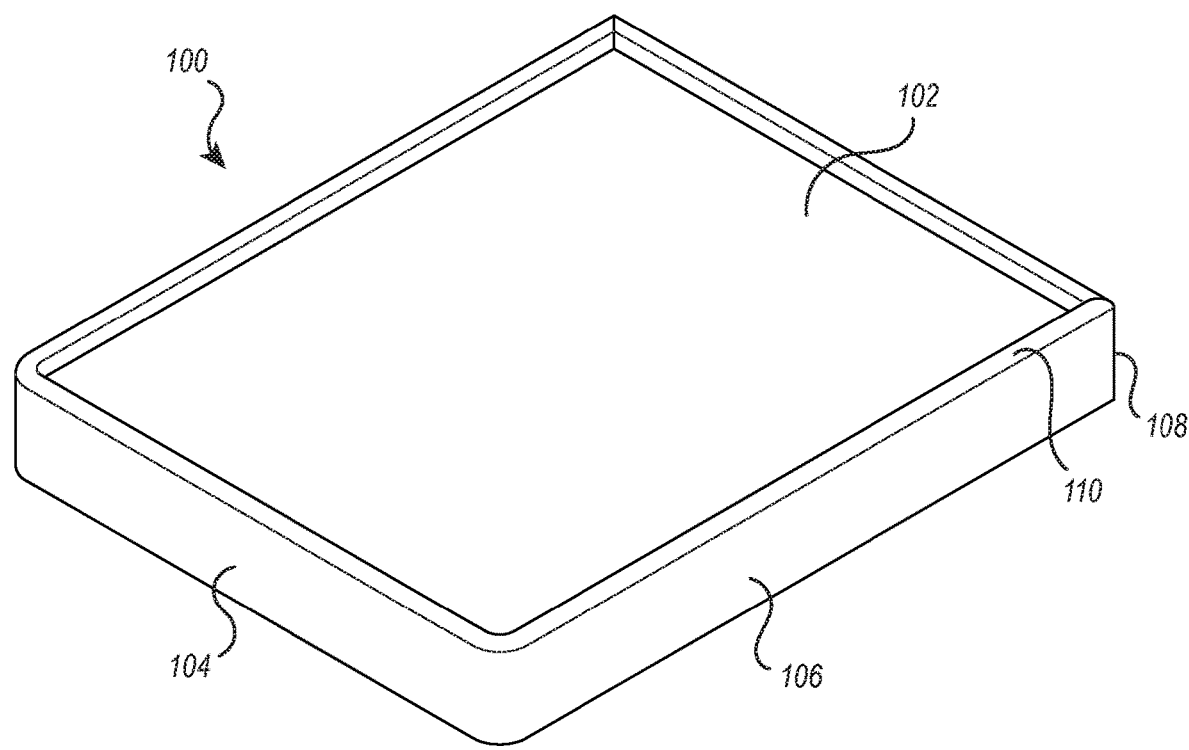
FIG. 3 illustrates a perspective view an exemplary embodiment of the cushion device of FIG. 2.

FIGS. 3-9 illustrate additional views of the cushion device 100. FIG. 3 illustrates a perspective view of the cushion device 100 of FIG. 2. The view of FIG. 3 shows the front portion 104, the two side portions 106 that connect to the front portion 104 and extend longitudinally therefrom, and the upper portion 102 supported by the front portion 104 and side portions 106. As described above, the back portion 108 (see FIG. 5) connects to the side portions 106 and is disposed opposite the front portion 104, and the upper portion 102 further comprises the rim 110 that extends vertically upward from the outer perimeter collectively defined by the front portion 104, the two side portions 106, and the back portion 108.

Figure 4:
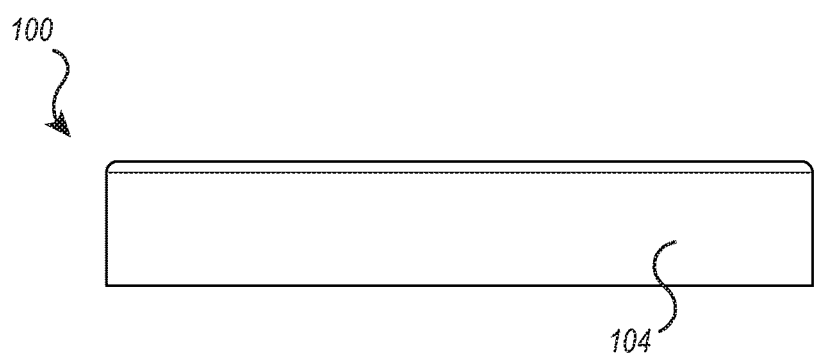
FIG. 4 illustrates a front view of the cushion device of FIG. 3.

FIG. 4 illustrates a front view of the cushion device 100. This view shows that the front portion 104 may have a rectangular shape with curved edges. A portion of the rim 110 is shown extending from a top line of the front portion 104. It should be appreciated that the front portion 104 may comprise any suitable height conducive to aiding in positioning a patient via the medical instrument stand. Alternatively, or additionally, the rim 110 may extend from the front portion to any height. In some embodiments, the rim 110 may extend variably from the perimeter defined by the front portion 104, side portions 106, and back portion 108. For example, the rim 110 adjacent to the front portion 104 may extend to a height that is greater than or less than a height to which the rim 110 extends from the side portions 106 or back portion 108.

Figure 5:
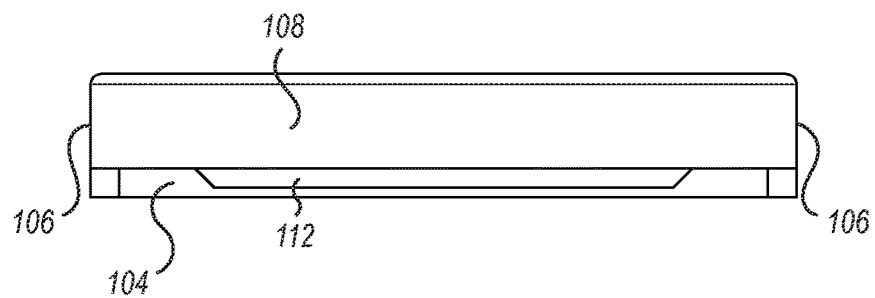
FIG. 5 illustrates a back view of the cushion device of FIG. 3.

FIG. 5 shows a rear view of the device. As shown in FIG. 5, the rear portion 108 may have a height that is smaller than a height of the front portion 104 and/or side portions 106. For example, the rear portion 108 may extend down from the top surface 102 a distance that is less than the distance the front portion 104 extends down from the top surface 102. In the illustrated embodiment, the rear portion 108 has a height that matches the thickness of the upper portion 102.

The open rear side allows the cushion device 100 to be easily slid onto the tray 12. For example, the cushion device 100 may be moved in a horizontal or somewhat horizontal fashion across the tray 12 and into position on top of the tray 12. Alternative embodiments may include a larger rear portion 108, such as one that extends lower and more closely aligns with the heights of the front portion 104 and side portions 106. Such an embodiment would more completely encase the perimeter of the tray 12 when positioned over the tray 12, but would likely have to be vertically lowered on top of the tray 12 rather than slid horizontally across the tray 12 and into position.

FIG. 5 also illustrates a contour portion 112 that connects to the upper portion 102 and extends downward therefrom. The contour portion 112 has a perimeter that sits within the perimeter of the upper portion 102 so that when the cushion device 100 is positioned on the stand 10, the upper surface of the tray 10 (or associated portion of the frame of the stand) can contact the bottom surface of the contour portion 112 while the rim portion 13 of the tray 12 extends up around the contour portion 112 to contact the bottom surface of the upper portion 102. This beneficially provides a more stable and conforming fit to standard tray geometry, and thereby serves to minimize or prevent sliding of the cushion device 100 upon the tray 12 or sagging of parts of the upper portion that otherwise would not initially contact the tray surface.

In some embodiments, the cushion device 100 may be configured to fit to the tray 12 of the stand 10 as discussed above. In some instances, the tray 12 may be removed from the stand 10, exposing an upper frame (not shown) that supports the tray 12 during use. In some embodiments, the cushion device 100 may be configured to straddle and fit over the upper frame of the stand 10 that supports the removeable tray 12. The uniquely designed cavity (i.e., contour portion 112) of the cushion device 100 offers versatility to securely fit to either the tray 12 or the upper frame for the tray 12.

The cushion device 100 may be configured with any suitable dimensions that allow a suitable fit to conventional medical instrument stand trays. Typically, the cushion device will have a length of about 20 to 30 inches, or about 21 to 29 inches, or about 22 to 28 inches, or about 23 to 27 inches, and will have a width that may be somewhat smaller than the length. For example, a width of about 18 to 28 inches, or about 19 to 26 inches, or about 20 to 24 inches. In some instances, the cushion device 100 may come in a small, regular, or large sizes (or any other number of varied sizes). In certain applications, a small sized cushion device 100 may fit trays 12 that measure 12"×19" up to 13"×19.625". A regular sized cushion device 100 may fit trays 12 that measure 16"×21" up to 16.75"×21.5". A large sized cushion device 100 may fit trays 12 that measure 20"×25".

The front portion 104 and/or side portions 106 may have a height of about 2 to 6 inches, such as about 4 inches, with a thickness of about 1 to 4 inches, more preferably about 1.5 to 3 inches or about 2 inches. Similarly, the upper portion 102 may have a thickness of about 1 to 4 inches, more preferably about 1.5 to 3 inches or about 2 inches. These thicknesses have beneficially shown to provide good cushioning and support without being so thick as to take up unnecessary space or make the device unnecessarily large and cumbersome.

The rim 110 may have a height of about 0.25 inches to 1 inch, or more preferably about 0.5 inches to beneficially function as an instrument/supply border without being overly high so as to disrupt the ability to use the cushion device to support a patient's limb. Similarly, the contour portion 112 may have a height of about 0.25 inches to 1 inch, more preferably about 0.5 inches to beneficially better match the contour of the underlying tray 12 and thereby provide a better fit of the cushion device 100 over the tray 12.

Figure 6:
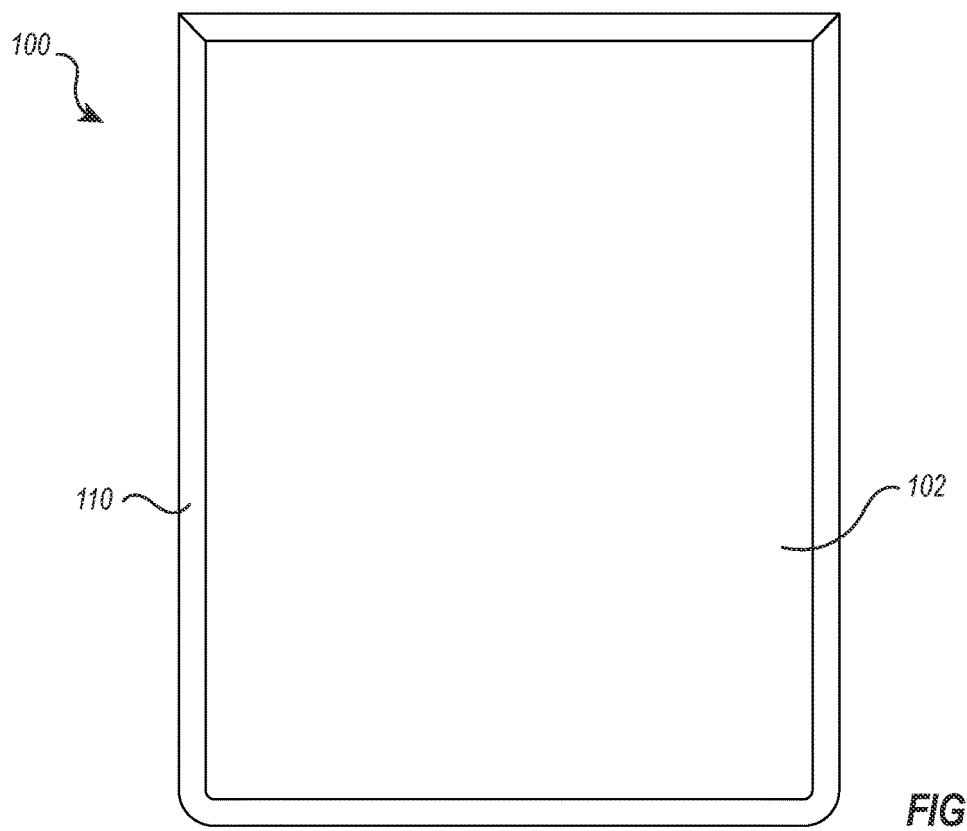
FIG. 6 illustrates a top view of the cushion device of FIG. 3.

FIG. 6 illustrates a top view of the cushion device 100 and shows the upper portion 102 and the rim 110 as described herein. It is anticipated that the upper portion 102 may form any shape that allows the cushion device 100 to encompass the tray 12 of the stand 10. In some embodiments, the upper portion 102 may comprise a shape that is different from the shape that is defined toward a bottom of the cushion device 100.

As illustrated, the upper portion 102 may have a smooth, uniform surface comprised of a soft layer memory foam. The upper portion 102 is configured to provide a comfortable and safe surface for patient positioning that helps avoid skin or nerve damage. The upper portion 102 may also be utilized as an effective operating surface for hand and wrist procedures. The upper portion 102 may further comprise a protective layer or skin that is configured to protect the memory foam or softer top layer foam from contaminants. The protective layer may comprise a material that is antimicrobial and/or offers a surface that is easier to clean than the foam layer.

The upper portion 102 is preferably formed from a soft, viscoelastic "memory" foam material to conform to the patient's body and prevent soft tissue injuries. Such memory foam materials typically have a 25% indentation load deflection (ILD) of about 10 to about 40 pounds, or more preferably about 20 to about 35 pounds. The foam material of the upper portion 102 may have a density of about 3 to about 9 pounds per cubic foot (PCF), preferably about 4 to about 8 PCF, or about 5 to about 7 PCF.

In some embodiments, one or more surfaces of the cushion device 100, such as the upper portion 102, may comprise ridges, indentations, patterning, depressions, or other features that assist in extremity positioning. Additionally, or alternatively, a removable layer configured to lay flush with the upper portion 102 may comprise the aforementioned features. For example, during hand and wrist procedures, a removable layer having a depression in the shape of a hand may be placed on top of the upper portion 102 to assist in stabilizing the hand during the procedure. In another example, the upper portion 102 may have a depression near the front portion 104 wherein the rim 110 also dips downward toward a middle region of the front portion 104 to facilitate a more comfortable positioning of an arm or a leg onto the cushion device 100. These features may be referred to as contour features.

Figure 7:
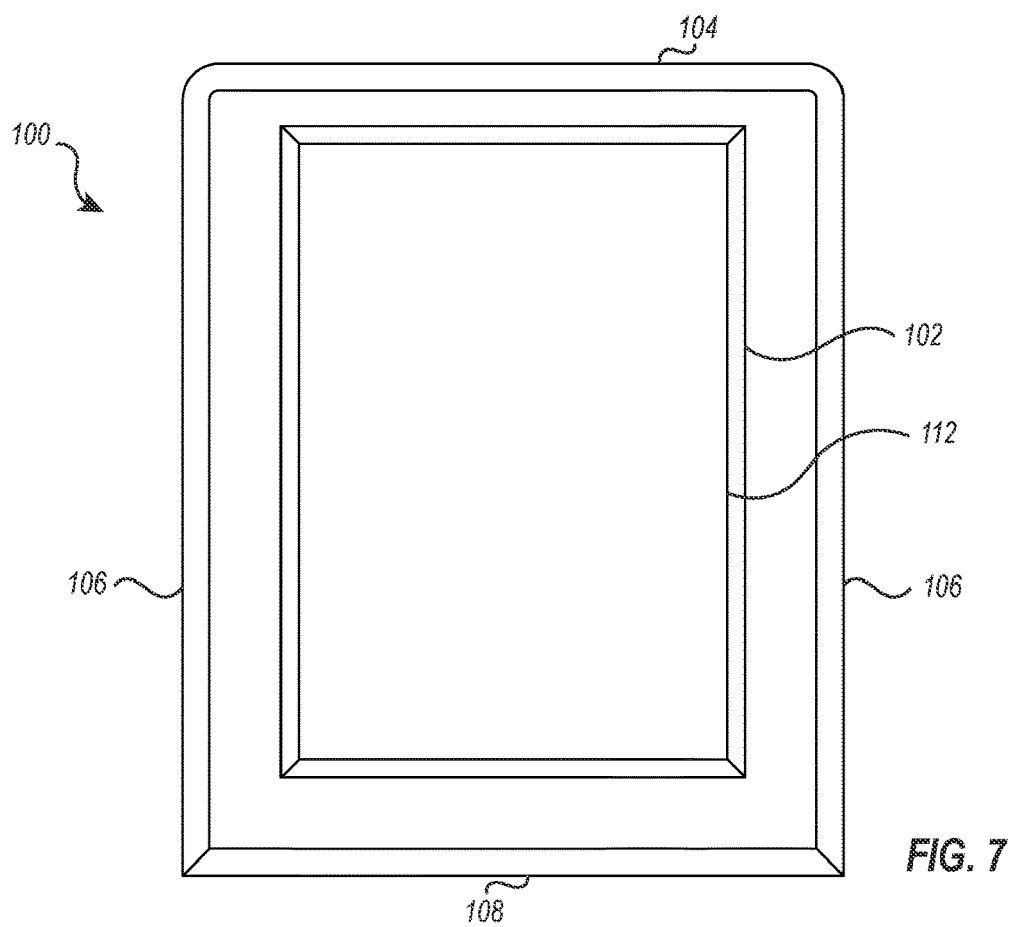
FIG. 7 illustrates a bottom view of the cushion device of FIG. 3.

FIG. 7 illustrates a bottom view of the cushion device 100 showing the front portion 104, two opposing side portions 106, and the back portion 108 which collectively define a rectangular shape to the cushion device 100. The contour portion 112 configured to fit flush with the tray 12 or engage with the frame of the stand 10 that supports the tray 12. As shown, the contour portion 112 comprises a rectangular shape; however, the contour portion 112 may comprise any shape that allows the cushion device 100 to be removably secured to the medical instrument stand 10. In some embodiments, the contour portion 112 may comprise a rectangular shape while the back portion 108, front portion 104, and side portions 106 may collectively define a shape different from that of the contour shape (e.g., circular, semi-circular, triangular, polygonal, etc). The contour portion 112 may have dimensions that allow it to suitably engage with a tray 12 of the medical device stand 10. Thus, the other portions of the cushion device 100 may comprise dimensions that are larger than those of the contour portion 112.

The contour portion 112 may be formed of the same material as the other components/portions of the device 100. Alternatively, the contour portion 112 may comprise a base foam layer that is more rigid in comparison to one or more other components/portions of the device 100, such as compared to a top layer of foam forming the upper portion 102. A more rigid base layer may be utilized to provide a stable operating and/or positioning surface. In some embodiments, the base is a cross-linked polyethylene foam.

The contour portion 112 may have an indentation load deflection (ILD) of at least about 50 pounds, more preferably at least about 75 pounds or at least about 100 pounds, such as an ILD within a range of about 50 to about 150 pounds, or about 75 to 135 pounds, or about 100 to about 120 pounds. The density of the contour portion 112 may be about 1 to about 4 PCF, such as about 1.5 to about 3 PCF. In some embodiments, the contour portion 112 may be formed from a #2 XLPE (cross-linked polyethylene) and/or other foam material(s) having similar density and ILD properties.

In some embodiments, a base portion of the cushion device may comprise a material that has sufficient firmness that allows it to provide some structural support to the cushion device 100 for use in as a stable operating surface but to also compress somewhat under typical patient weight. Thus, a layer of the cushion device 100 may be formed from #2 XLPE and/or other foam material(s) having similar density and ILD properties.

Figure 8:
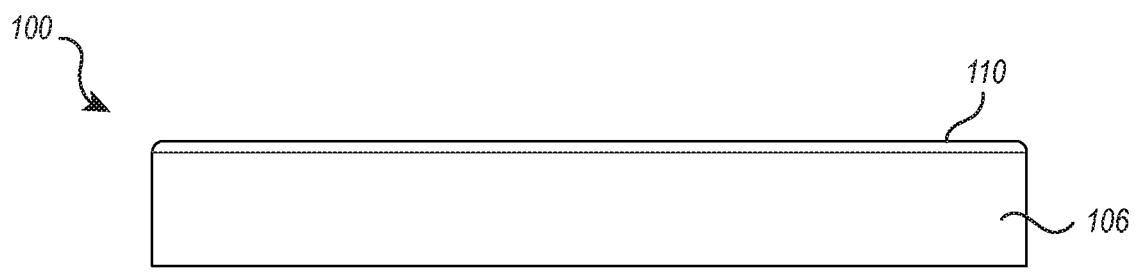
FIGS. 8 and 9 illustrate opposing side views of the cushion device of FIG. 3.
Figure 9:
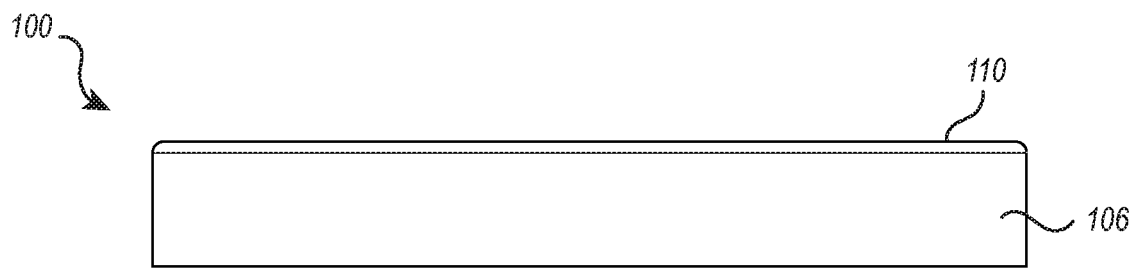

FIGS. 8 and 9 illustrate opposing side views of the cushion device 100, showing side portions 106 and showing rim 110 extending vertically upward from side portions 106. The rim 110 may extend from one side portion 106 (see FIG. 8) to a height greater or less than the height to which the rim 110 extends from the opposite side portion 106 (see FIG. 9).

In some embodiments, the cushion device 100 is configured with multiple layers of foam that may have different density. Additionally, or alternatively, the cushion device 100 may comprise a single layer or multiple layers of uniform density foam.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A cushion device configured for placement on a medical instrument stand, the cushion device comprising:
   an upper portion having a front side, a rear side, first and second longitudinal sides, an upper surface, and a bottom surface;
   a front portion connected to the front side of the upper portion and extending downwards therefrom and below the bottom surface;
   first and second side portions each connected respectively to the first and second longitudinal sides of the upper portion and extending downward therefrom and below the bottom surface;
   a hollow receptacle defined by an inner surface of the front portion extending downwards and below the upper portion, opposing inner surfaces of the first and second side portions extending downwards and below the upper portion, and the bottom surface of the upper portion, wherein the hollow receptacle is configured in size and shape to fit over and receive therein a medical instrument tray or portion of a frame of a medical instrument stand associated with a medical instrument tray; and
   a contour portion connected to the bottom surface of the upper portion and extending downward from the bottom surface.

2. The cushion device of claim 1, further comprising a rim disposed on the upper portion and extending upward from the upper surface of the upper portion and extending along at least a portion of a perimeter of the upper surface of the upper portion.

3. The cushion device of claim 2, wherein the rim has a rounded cross-sectional profile.

4. The cushion device of claim 1, wherein a rear side of the cushion device has an open gap that enables the cushion device to be slid horizontally onto a medical instrument tray.

5. The cushion device of claim 1, wherein the contour portion has a perimeter smaller than a perimeter of the upper portion in order for an outer surface of the contour portion to partially define the hollow receptacle.

6. The cushion device of claim 1, wherein the front portion and/or the first and second side portions extend farther downward from the bottom surface of the upper portion than the contour portion in order to at least partially enclose an outer perimeter of a medical instrument tray.

7. The cushion device of claim 1, wherein the cushion device is formed from a foam material.

8. The cushion device of claim 7, wherein the cushion device includes a water-resistant polymer coating on the foam material.

9. The cushion device of claim 1, wherein the upper portion of the cushion device comprises a foam of lower firmness than the contour portion of the cushion device.

10. The cushion device of claim 1, wherein the cushion device has a length of about 20 to 30 inches.

11. The cushion device of claim 1, wherein the cushion device has a width that is smaller than a length.

12. The cushion device of claim 1, wherein the cushion device has a width of about 18 to 28 inches.

13. The cushion device of claim 1, wherein the front portion and/or side portions have a height of about 2 to 6 inches.

14. The cushion device of claim 1, wherein the upper portion has a thickness of about 1 to 4 inches.

15. The cushion device of claim 1, wherein the upper portion further comprises at least one contour feature disposed on an upper surface of the upper portion.

16. The cushion device of claim 1, wherein the contour portion has a perimeter so as to fit within a rim portion of a medical instrument tray.

17. A method of cushioning a medical instrument tray, comprising:
   providing a cushion device, the cushion device including
      an upper portion having a front side, a rear side, first and second longitudinal sides, an upper surface, a bottom surface;
      a front portion connected to the front side of the upper portion and extending downwards therefrom and below the bottom surface;
      a back portion connected to the rear side of the upper portion and extending downwards therefrom and below the bottom surface;
      first and second side portions each connected respectively to the first and second longitudinal sides of the upper portion and extending downward therefrom and below the bottom surface;
      a hollow receptacle defined by opposing inner surfaces of the front portion and the back portion extending downwards and below the upper portion, opposing inner surfaces of the first and second side portions extending downwards and below the upper portion, and the bottom surface of the upper portion, wherein the hollow receptacle is configured in size and shape to fit over, receive therein, and enclose a medical instrument tray or portion of a frame of a medical instrument stand associated with the medical instrument tray; and
      a contour portion connected to the bottom surface of the upper portion and extending downward from the bottom surface; and
   positioning the cushion device so that the hollow receptacle fits over and receives therein the medical instrument tray or a portion of the frame of the medical instrument stand associated with the medical instrument tray.

18. The method of claim 17, further comprising positioning a patient's limb upon the cushion device while the cushion device is supported by the medical instrument stand.

19. A cushion device configured for placement on a medical instrument stand, the cushion device comprising:
   an upper portion having a front side, a rear side, first and second longitudinal sides, an upper surface, a bottom surface, and a raised rim extending vertically above the front side, the rear side, the first and second longitudinal sides, and the upper surface, the raised rim providing a raised wall extending above and around an entire perimeter of the upper portion;
   a front portion connected to the front side of the upper portion and extending downwards therefrom; and
   first and second side portions each connected respectively to the first and second longitudinal sides of the upper portion and extending downward therefrom, wherein a hollow receptacle is defined by the front portion, the first and second side portions, and by the bottom surface of the upper portion, the hollow receptacle being configured in size and shape to receive a medical instrument tray or portion of a frame of a medical instrument stand associated with a medical instrument tray, and wherein a rear side of the cushion device has an open gap that enables the cushion device to be slid horizontally onto a medical instrument tray.

20. The cushion device of claim 19, further comprising a contour portion connected to the bottom surface of the upper portion and extending downward from the bottom surface.

\* \* \* \* \*